(12) United States Patent
Perrier et al.

(10) Patent No.: US 6,524,595 B1
(45) Date of Patent: Feb. 25, 2003

(54) CYCLODEXTRINS PREFERENTIALLY SUBSTITUTED ON THEIR PRIMARY FACE BY ACID OR AMINE FUNCTIONS

(75) Inventors: Eric Perrier, Les Cotes D'Arey (FR); Nicolas Terry, Saint Jean de Bournay (FR); Delphine Rival, Ternay (FR); Anthony William Coleman, Caluire (FR)

(73) Assignee: Coletica, Lyons (FR)

( * ) Notice: Subject to any disclaimer, the term of this patent is extended or adjusted under 35 U.S.C. 154(b) by 0 days.

(21) Appl. No.: 09/613,773

(22) Filed: Jul. 11, 2000

(30) Foreign Application Priority Data

May 12, 2000 (FR) .............................................. 00 06102

(51) Int. Cl.$^7$ .......................... A61K 7/00; A61K 39/00; A61K 9/50; A61K 31/715; C08B 37/00
(52) U.S. Cl. .................... 424/401; 424/184.1; 424/499; 514/58; 536/18.7
(58) Field of Search ................................ 424/401, 499, 424/184.1; 514/58; 536/18.7

(56) References Cited

U.S. PATENT DOCUMENTS

| | | | |
|---|---|---|---|
| 3,565,887 A | | 2/1971 | Parmerter et al. |
| 5,068,227 A | * | 11/1991 | Weinshenker ................ 514/58 |
| 5,631,244 A | | 5/1997 | Galons et al. |
| 5,718,905 A | * | 2/1998 | Skiba et al. ................ 424/499 |
| 5,854,225 A | | 12/1998 | Richard et al. |
| 5,959,089 A | * | 9/1999 | Hannessian ................ 536/18.7 |
| 6,045,812 A | * | 4/2000 | Richard et al. ............. 424/401 |
| 6,165,995 A | | 12/2000 | Hilgers |
| 6,328,965 B1 | | 12/2001 | Hilgers |

FOREIGN PATENT DOCUMENTS

| | | | |
|---|---|---|---|
| EP | 0 636 634 | | 2/1995 |
| EP | 0 773 229 | | 5/1997 |
| FR | 2 681 868 | | 4/1993 |
| JP | 52-130904 | | 11/1977 |
| JP | 56-139409 | | 10/1981 |
| WO | WO 93/25194 | | 12/1993 |
| WO | WO 96/20222 | | 7/1996 |
| WO | WO-97/04747 | * | 2/1997 |
| WO | WO-99/43359 | * | 9/1999 |

OTHER PUBLICATIONS

Hironori et al. "Cyclodextrin Derivatives". Chemical Abstracts, vol. 81, No. 1 (1975). Abstract No. 4533s & JP 07 485015 A. Tanabe Seiyaku Co. Aug. 15 1974.

Ogawa et al. "A New Approach to Regioselective Acylation of Polyhydroxy Compounds." Carbohydrate Research, vol. 55 (1977): pp. c1–c6.

Zhang et al. "Formation of Amphiphilic Cyclodextrins via Hydrophobic Esterification at the Secondary Hydroxyl Face," Tetrahedron Letters, vol. 32, No. 24 (1991): pp. 2769–2770.

\* cited by examiner

Primary Examiner—Sreeni Padmanabhan
Assistant Examiner—Michael A. Willis
(74) Attorney, Agent, or Firm—Merchant & Gould P.C.

(57) ABSTRACT

Non-hydroxyalkylated cyclodextrins are disclosed wherein at least one primary alcohol function ($CH_2OH$) is substituted, the —OH portion being replaced by a substituent with formula —O—CO—R or —$NR_1R_2$, where:

R, $R_1$ and $R_2$ independently represent a linear or cyclic, saturated or unsaturated, hydroxylated or non-hydroxylated alkyl group containing 1 to 30 carbon atoms, preferably 1 to 22 carbon atoms, more preferably a fatty chain containing 2 to 22 carbon atoms. These cyclodextrins are used as vectors for at least one active ingredient, in particular to encourage tissue penetration, in a cosmetic application, or for the production of pharmaceutical compositions, in particular dermopharmaceuticals.

17 Claims, 3 Drawing Sheets

Observation of nanoparticles using atomic force microscopes

Observation of nanoparticles using atomic force microscopes

Observation of nanoparticles using atomic force microscopes

Observation of nanoparticles in a carbopol gel after 18 days at 23°C

CYCLODEXTRINS PREFERENTIALLY SUBSTITUTED ON THEIR PRIMARY FACE BY ACID OR AMINE FUNCTIONS

PRIOR ART

The use of alpha, beta or gamma cyclodextrins as cage molecules capable of trapping hydrophobic molecules has been particularly well described: trapping of vitamin E (Japanese patent JP56/139409), vitamin D3 (JP52/130904) for example, but also menthol, fragrances, essential oils, etc.

However, the use of such cyclodextrins poses a certain number of problems: in particular, their solubility in an aqueous phase is very poor (in particular beta cyclodextrin) and their solubility in a hydrophobic phase is almost zero. Faced with such a problem, a first strategy consists of producing derivatives of such cyclodextrins to increase the solubility of the molecules in aqueous phases:

using methyl, dimethyl, polymethyl derivatives,
using hydroxyalkylated derivatives (European patent EP-A1-0 636 634),
using sulfate or phosphate derivatives, or to increase their solubility in oily phases:

using lipophilic derivatives (U.S. Pat. No. 3,565,887),
using lipophilic hydroxyalkylated derivatives (EP-A1-0 773 229),
using cyclodextrins monosubstituted exclusively on their primary face (reaction with a primary alcohol function) or cyclodextrins completely substituted exclusively on their secondary face (reaction with all of the secondary alcohol functions) (French patent FR-A-2 681 868).

Further, a second strategy has slowly been developing in which amphiphilic structures are synthesized from cyclodextrins, which structures enable the cyclodextrins to arrange themselves into micelles or nanoparticles:

the products described in French patent FR-A-2 681 868 can thus form nanoparticles,
the products described in European patent EP-A-0 773 229 can form nanoparticles,
it is also possible to produce the nanoparticles which are described in International patent application WO 93/25194 from cyclodextrins completely substituted on their secondary face, synthesized in accordance with Zhang and al. (Zhang, Ling, Coleman, Parrot-Lopez, Galons, Tetrahedron Letters 32 (24) 2769–2770, 1991).

The inventors have unexpectedly discovered that, in contrast to current wisdom, it is possible to produce nanoparticles from amphiphilic cyclodextrins which are mono- or multi-substituted, preferably on their primary face.

The skilled person will always aim to substitute the secondary face of cyclodextrins to produce nanoparticles, as the geometry of nanoparticles substituted on their secondary face is highly favorable to the formation of curved shapes (which enable such structures to organize themselves into nanoparticles), while the geometry of cyclodextrins substituted on their primary face is highly unfavorable to the formation of nanoparticles. Thus amphiphilic cyclodextrins for the production of nanoparticles are synthesized by blocking the primary alcohol functions which are chemically more reactive, then alkylating the secondary alcohol functions, and unblocking the primary alcohol functions in a third stage (Zhang et al., 1991 and also FR-A-2 681 868 and EP-A-0 773 229). This sequence of reactions causes problems with yield and with the industrialization of processes, which limits their use. Commercial use is currently non-existent.

The inventors have succeeded in producing nanoparticles from non-hydroxyalkylated cyclodextrins, mono- or di-substituted on their primary face which was completely unexpected, with many fields of application in the areas of encapsulating molecules of cosmetic, pharmaceutical, or agro-industrial interest, and of modulating the penetration of encapsulated active ingredients into tissues, cells, etc. . . .

The inventors have also discovered that the amphiphilic cyclodextrins of the invention have the capacity to promote penetration of active ingredients in a manner which is spectacularly stronger than other vectors which have been far more widely studied, namely liposomes.

For this reason, the targeting properties of these amphiphilic cyclodextrin molecules (which may or may not be in the form of nanoparticles, included in phospholipid double layers or not) have become extremely interesting, and chemical modifications of these cyclodextrins have been made to allow such targeting.

In particular, the invention enables molecules with selective affinities to be grafted onto the amphiphilic cyclodextrins of the invention, via a spacer arm which may or may not remain present in the chemical structure of the molecule formed.

The invention also renders possible the production of completely novel chemical entities of real industrial and economic significance in fields as varied as cosmetics, pharmacy, agro-industry, etc. . . .

OBJECTS AND SUMMARY OF THE INVENTION

Thus a principal aim of the invention is to solve the novel technical problem consisting of providing novel chemical entities which can be used in cosmetics, pharmacy, agro-industry and in the food industry.

A further principal aim of the present invention is to solve a novel technical problem consisting of providing a solution which can provide novel chemical cyclodextrin entities which can form nanoparticles or micelles of very small dimensions, in particular nanoparticles.

A still further principal aim of the present invention is to solve the novel technical problem consisting of providing novel chemical cyclodextrin entities which are easy to synthesize and have a good synthesis yield, thus enabling such novel chemical entities to be used on an industrial scale.

A yet still further principal aim of the present invention is to solve the novel technical problem consisting of providing novel chemical cyclodextrin entities which can trap or encapsulate molecules of cosmetic, pharmaceutical or agro-industrial interest to enable the penetration of the encapsulated active ingredients into tissue, cells etc. to be modulated.

A yet still further principal aim of the present invention is to solve the novel technical problem consisting of providing a solution which can provide novel chemical cyclodextrin entities with the capacity to promote penetration of active ingredients in a manner which is spectacularly stronger than other vectors which have been more widely studied, namely liposomes.

A yet still further principal aim of the present invention is to solve the novel technical problem consisting of providing novel chemical cyclodextrin entities which can graft molecules with selective affinities directly or via a spacer arm which remains in the chemical structure of the molecule thus formed.

All of these technical problems are solved for the first time by the present invention in a particularly simple fashion, with excellent yields, rendering the solution of the invention useful on an industrial and on a commercial scale, in fields as varied as the cosmetics industry, in pharmacy, in the agro-industry and in the food industry.

Thus in a first aspect, the invention concerns the use of non-hydroxyalkylated cyclodextrins wherein at least one primary alcohol function (CH$_2$OH) is substituted, the —OH portion being replaced by a substituent with formula —O—C(=O)—R or —NR$_1$R$_2$, where:

R, R$_1$ and R$_2$ independently represent a linear or cyclic, saturated or unsaturated, hydroxylated or non-hydroxylated hydrocarbon radical containing 1 to 30 carbon atoms, preferably 1 to 22 carbon atoms, more preferably a fatty chain 2 to 22 carbon atoms;

to encourage tissue penetration, either for a cosmetic application or for producing pharmaceutical compositions, in particular dermopharmaceutical compositions; provided that when the substituent has formula —O—CO—R, the esterified non-hydroxyalkylated cyclodextrins are used as a vector for at least one active ingredient.

In a second aspect, the present invention concerns the use of non-hydroxyalkylated cyclodextrins in the form of micelles or nanoparticles, wherein at least one primary alcohol function (CH$_2$OH) is substituted, the —OH portion being replaced by a substituent with formula —O—C(=O)—R or —NR$_1$R$_2$, where:

R, R$_1$ and R$_2$ independently represent a linear or cyclic, saturated or unsaturated, hydroxylated or non-hydroxylated hydrocarbon radical containing 1 to 30 carbon atoms, preferably 1 to 22 carbon atoms, more preferably a fatty chain 2 to 22 carbon atoms;

to encourage tissue penetration, either for a cosmetic application or for producing pharmaceutical compositions, in particular dermopharmaceutical compositions, preferably as a vector for at least one active ingredient.

It should be noted that cyclodextrins have primary alcohols on their primary face defined by the short base of their trapezoidal shape, and secondary alcohol functions on their secondary face defined by the long base of said trapezoid (conventional structure of cyclodextrin). The invention preferably produces substitution on the primary alcohol functions of the primary face of the cyclodextrins. The skilled person will know that each glucose unit of a cyclodextrin comprises two secondary alcohols and one primary alcohol.

Advantageously, the substituted cyclodextrin has the following chemical formula:

$$CD(OH)_w(P)_x(X)_y(M)_z$$

where:

CD represents a structure based on a non-hydroxyalkylated cyclodextrin without its hydroxyl groups, in particular α, β or γ-cyclodextrin, OH represents the free hydroxyl groups of the cyclodextrin, x and z independently represent a whole number in the range 0 to 17, or in the range 0 to 20, or in the range 0 to 23, when the cyclodextrins are respectively α, β or γ in type;

y represents a whole number in the range 1 to 18, or in the range 1 to 21, or in the range 1 to 24 when the cyclodextrins are respectively α, β or γ in type, w represents a whole number such that the sum (w+x+y+z) is equal to 18, 21 or 24 when the cyclodextrins are respectively α, β or γ in type;

X represents a substituent with formula —O—C(=O)—R or —N(R$_1$R$_2$) defined below, replacing the —OH portion of at least one primary alcohol function and optionally at least one secondary alcohol function;

P represents a radical substituting a primary or secondary hydroxyl group, in particular a sulfate, phosphate, methyl, ose or oside substituent;

when at least one X represents —NR$_1$R$_2$, —NR$_1$R$_2$ is a radical substituting at least one primary hydroxyl group and optionally at least one secondary hydroxyl group, or the two, attached to the cyclodextrin skeleton, where R$_1$ and R$_2$ independently represent a linear or cyclic, saturated or unsaturated, hydroxylated or non-hydroxylated hydrocarbon radical containing 1 to 30 carbon atoms, preferably 1 to 22 carbon atoms, more preferably a fatty chain 2 to 22 carbon atoms; preferably when X represents NR$_1$R$_2$, 1% to 100% of the primary cyclodextrin hydroxyl groups are substituted by the amino group NR$_1$R$_2$;

when at least one X represents —O—C(=O)—R, —O—C(=O)—R is a radical substituting at least one primary hydroxyl group, and optionally at least one secondary hydroxyl group, or the two, attached to the cyclodextrin skeleton, where R represents a linear or cyclic, saturated or unsaturated, hydroxylated or non-hydroxylated hydrocarbon radical containing 1 to 30 carbon atoms, preferably 1 to 22 carbon atoms, more preferably a fatty chain containing 2 to 22 carbon atoms; preferably, when X represents —O—COR, 1% to 100% of the primary hydroxyl groups of the cyclodextrins are substituted by the ester group —O—COR;

(X)$_y$ can represent mixtures of —NR$_1$R$_2$ or —OCOR groups substituting at least one primary hydroxyl group and optionally at least one secondary hydroxyl group, or the two;

M is a substituent for at least one primary or secondary alcohol function or the two of the cyclodextrin, M is a functional group G$_1$ or a specific radical G$_2$, either directly substituting a primary or secondary alcohol function of the cyclodextrin, or indirectly substituting said primary or secondary alcohol function via a spacer arm W, where:

W is a spacer arm containing 1 to 20 carbon atoms, including the groups selected from the following functions and their derivatives: acid, sulfonic and phosphoric acid, alkanoyl, alkenyl, alkynyl, aldehyde, amine, amide, azide, acid anhydride, ketone, isocyanate, phenyl, hydroxyl, epoxy, ester, imide, amidine, halide, nitro, nitrites, peroxides, organometallic derivatives, sulfur-containing derivatives;

G$_1$ represents at least one of the following functions and its derivatives: acid, sulfonic and phosphoric acid, alkanoyl, alkenyl, alkynyl, aldehyde, amine, amide, azide, acid anhydride, ketone, isocyanate, phenyl, hydroxyl, epoxy, ester, imide, amidine, halide, nitro, nitrites, peroxides, organometallic derivatives, sulfur-containing derivatives; and G$_2$ represents at least one of the following compounds or its derivatives selected from the group consisting of a sugar, a polyol, an oligosaccharide, a polysaccharide, a lectin, an amino acid, a peptide, a protein, an antibody, a nucleotide, a nucleoside, an oligonucleotide, an oligonucleoside, a chromophore, a polymer, a sterol, a steroid, a hormone, a flavonoid, a terpene, caffeine, theophylline and their derivatives, nicotine and its derivatives, a vitamin, a vitamin ester, cholesterol, a phospholipid, a glycolipid, a sphingolipid, a ceramid, a triglyceride, a natural or synthetic polyphenol, an essential oil, a flavoring, a fragrance, a dye, or a cosmetically, dermopharmaceutically, pharmaceutically or alimentarily active substance.

In the present description and claims, the expression:

"a substituent of at least one primary or secondary alcohol function" means substitution of either a primary alcohol group carried by a primary alcohol function —CH$_2$OH, or of a secondary alcohol group carried by the secondary alcohol function —CHOH, as is well understood by the skilled person, "at least one primary or secondary hydroxyl function" means a primary or secondary hydroxyl function present in a primary alcohol function —CH$_2$OH or a secondary alcohol function —CHOH attached respectively to the cyclodextrin skeleton.

In a particular embodiment, said cyclodextrin is a cyclodextrin substituted by 1 to 18, 1 to 21 or 1 to 24 lauric fatty chains when the cyclodextrins are respectively type α, β or γ, in particular 2 or 3 lauric chains, or 7, 8 or 9 lauric chains.

In a particular embodiment, the above cyclodextrin derivative is a cyclodextrin substituted by at least one hexanoyl substituent on at least one primary hydroxyl function, in other words a cyclodextrin substituted by 1 to 18, 1 to 21 or 1 to 24 fatty hexanoic chains when the cyclodextrins are respectively type α, β or γ, in particular 6 to 10 hexanoic chains, principally 7, 8 and 9 hexanoic acid chains.

A further particular embodiment is constituted by a substituted cyclodextrin wherein at least one primary hydroxyl function is substituted by at least one N,N-dipentylamine group.

In yet another particular embodiment of the invention, the cyclodextrin derivative is further substituted by at least one substituent selected from the group formed by 4-nitrophenylformate; ethyloxalic; chloroacetyl; succinic; oxalic sulfonic; N-(2-aminoethyl)lactonamide.

In yet another particular embodiment, the cyclodextrin derivative is a β-cyclodextrin, in particular a heptakis (6-deoxy-6-(N,N-dipentylamino))-β-cyclodextrin.

In yet another advantageous embodiment, said cyclodextrin comprises at least one primary or secondary hydroxyl flinction substituted by a functional group G$_1$ or a radical G$_2$ as cited above selected from the following compounds or functions or their derivatives selected from the group formed by acid, sulfonic and phosphoric acid, alkanoyl, alkenyl, alkynyl, aldehyde, amine, amide, azide, an anhydride, ketone, isocyanate, phenyl, hydroxyl, epoxy, ester, imide, amidine, halide, nitro, nitriles, peroxides, organometallic derivatives, sulfur-containing derivatives, a sugar, an oligosaccharide, a polysaccharide, an amino acid, a peptide, a protein, a nucleotide, an oligonucleotide, a nucleoside, an oligonucleoside, a chromophore, a polymer, a steroid, a vitamin or another active ingredient.

In a yet still further particularly advantageous embodiment, the cavity of the substituted cyclodextrin comprises an active ingredient which is in particular cosmetically, dermopharmaceutically, pharmaceutically, or alimentarily acceptable, encapsulated therein and/or covalently bonded therewith.

In an advantageous characteristic of the invention, the active ingredient is selected from the group formed by at least one sugar, a polyol, an oligosaccharide, a polysaccharide, an amino acid, a peptide, a protein, a nucleotide, a nucleoside, an oligonucleotide, an oligonucleoside, a chromophore, a polymer, a sterol, a steroid, a hormone, a flavonoid, a terpene, caffeine, theophylline and their derivatives, nicotine and its derivatives, a vitamin, a vitamin ester, cholesterol, a phospholipid, a glycolipid, a sphingolipid, a ceramid, a triglyceride, a natural or synthetic polyphenol, an essential oil, a flavoring, a fragrance, a dye, or a cosmetically, dermopharmaceutically, pharmaceutically, or alimentarily acceptable excipient.

In a further particular embodiment of the invention, said cyclodextrin comprises at least a second graft, in which said functional group G$_1$ or said radical G$_2$, directly or indirectly substituting the primary or secondary alcohol function, is different from that possibly used for the first graft. Particular examples of at least one second graft are a second graft on at least one alcohol function of the primary face of the cyclodextrin molecule and/or on at least one alcohol function of the secondary face of the cyclodextrin molecule, selected from the group formed by:

one or more 4-nitrophenylformate groups;

one or more ethyloxalic groups;

one or more chloroacetyl groups;

one or more succinic acid groups;

one or more oxalic acid groups;

one or more sulfonic acid groups;

one or more ethylene diamine groups;

one or more lactone groups, in particular N-(2-amino ethyl)lactonamide.

In a third aspect, the present invention encompasses micelles or nanoparticles based on cyclodextrin derivatives, wherein they are prepared from a non-hydroxyalkylated cyclodextrin derivative as defined above or as described in the following description including the examples, supplemented by the figures, which in their generality form an integral part of the present invention.

The characteristic advantages of micelles or nanoparticles are defined in the sub-claims which are incorporated into the description by reference.

In a fourth aspect, the present invention encompasses a composition selected from the group formed by a cosmetic, dermopharmaceutical, pharmaceutical or agro-alimentary composition, wherein the composition comprises at least one cyclodextrin, in particular in the form of micelles or de nanoparticles, as defined above or as described in the following description as a whole and including the examples supplemented by the figures, in combination with a cosmetically, dermopharmaceutically or pharmaceutically acceptable excipient, vehicle or support or an excipient, vehicle or support which is alimentarily acceptable, this excipient being in particular composed of phospholipids, for example lecithin, surfactants or cationic lipids.

In a fifth aspect, the invention encompasses a composition selected from the group formed by a cosmetic, dermopharmaceutical, pharmaceutical or agro-alimentary composition, wherein the composition comprises at least one micelle or nanoparticle as defined above or resulting from the following description including the examples supplemented by the figures, in combination with a cosmetically, dermopharmaceutically or pharmaceutically acceptable excipient, vehicle or support or an excipient, vehicle or support which is alimentarily acceptable, this excipient being in particular composed of phospholipids, for example lecithin, surfactants or cationic lipids.

The advantageous characteristics of these compositions are also shown in the composition sub-claims which are entirely incorporated into the description by reference.

In a sixth aspect, the present invention encompasses cyclodextrin derivatives as defined above which are novel with respect to any prior art. In particular, cyclodextrin derivatives in which:

- either at least one X represents —N(R$_1$R$_2$) of a primary alcohol;
- or at least one X represents —N(R$_1$R$_2$) combined with at least one —O—C(=O)—R;
- or at least one X represents —O—C(=O)—R with at least one radical P and/or at least one radical M substituting at least one primary alcohol and/or secondary alcohol; are novel and are claimed as such.

A preferred group of novel cyclodextrin derivatives is constituted by cyclodextrin derivatives in which at least one substituent P or M is present.

Still more preferred derivatives are those in which, in addition to the primary hydroxyl function substituted as defined in the present description and claims, at least one secondary hydroxyl function is substituted by at least one substituent P or M as defined in the present description and claims.

Cyclodextrin derivatives in which the substituted cyclodextrin cavity comprises an active ingredient, in particular cosmetically, dermopharmaceutically, pharmaceutically or alimentarily acceptable, encapsulated therein and/or covalently bonded thereto, also constitute novel cyclodextrin derivatives claimed as they are. Examples of active ingredients as defined in the present description and claims are also claimed as forming an integral portion of the present invention.

In a seventh aspect, the present invention still further encompasses a process for producing novel cyclodextrin derivatives as defined above, wherein the process comprises the following synthesis steps, preferably in succession:

a) firstly, substituting at least one primary hydroxyl function of a cyclodextrin by a chemical molecule capable of providing a substituent with formula —O—C(=O)—R or —NR$_1$R$_2$, having the meanings defined in the present description and claims;

b) optionally, substituting at least one primary or secondary hydroxyl function or both with a radical M or P as defined in the present description and claims.

In an advantageous implementation of this process, when a substituent radical P is present, at least one primary or secondary hydroxyl group is substituted by a sulfate, phosphate, methyl, ose or oside substituent.

The term "ose or oside" as used in the present invention means the entire family of oses or osides, which are well known to the skilled person, in particular sugars, oligosaccharides, polysaccharides, nucleotides, nucleosides, oligonucleotides, and oligonucleosides.

The reaction conditions are well known to the skilled person.

As an example, the reaction conditions of U.S. Pat. No. 3,565,887 can be applied to prepare cyclodextrin derivatives with esterified primary alcohol functions.

It is also possible to apply the reaction conditions defined for cyclodextrin substitution described in FR-A-2 680 868 or EP-A-0 773 229 or WO-A-93/25194.

Further reaction conditions will also be made clear in the examples and description below.

In an eighth aspect, the invention encompasses a process for producing micelles or nanoparticles comprising cyclodextrin derivatives of the present invention, as defined above or resulting from the following description incorporating the examples supplemented by the figures, wherein the process comprises an organic phase into which the substituted cyclodextrins are introduced and a principally aqueous phase. These two phases are mixed under controlled flow rate, stirring and temperature parameters. Stirring can be either mechanical or sonic.

In a ninth aspect, the present invention also encompasses a cosmetic care method, wherein a cosmetically effective quantity of at least one cyclodextrin derivative as defined above in the context of any one of its aspects or as resulting from the following description made with reference to the examples, optionally in a cosmetically acceptable excipient, is applied to a zone of the body of a person requiring the care.

In the context of this cosmetic care, the cyclodextrin derivatives unexpectedly encourages cutaneous penetration, in a manner which is improved over liposomes.

In a tenth aspect, the invention encompasses a therapeutic treatment method wherein a pharmaceutically effective quantity of at least one cyclodextrin derivative as defined in the present invention in any one of its aspects, optionally in a pharmaceutically acceptable excipient, is administered to a patient. In the context of this therapeutic treatment, it should be clear that the cyclodextrins of the invention can improve the bioavailability of the pharmaceutically active substances encapsulated by said substituted cyclodextrins or covalently contained by them.

BRIEF DESCRIPTION OF THE DRAWINGS

Other aims, characteristics and advantages of the invention will become clear from the following description made with reference to the examples below, firstly concerning synthesis of a novel chemical cyclodextrin entity in part I then examples of forming nanoparticles in part II, and then activity tests, given simply by way of illustration but which in no way limit the scope of the invention.

In the figures.

MORE DETAILED DESCRIPTION

Figure 1:
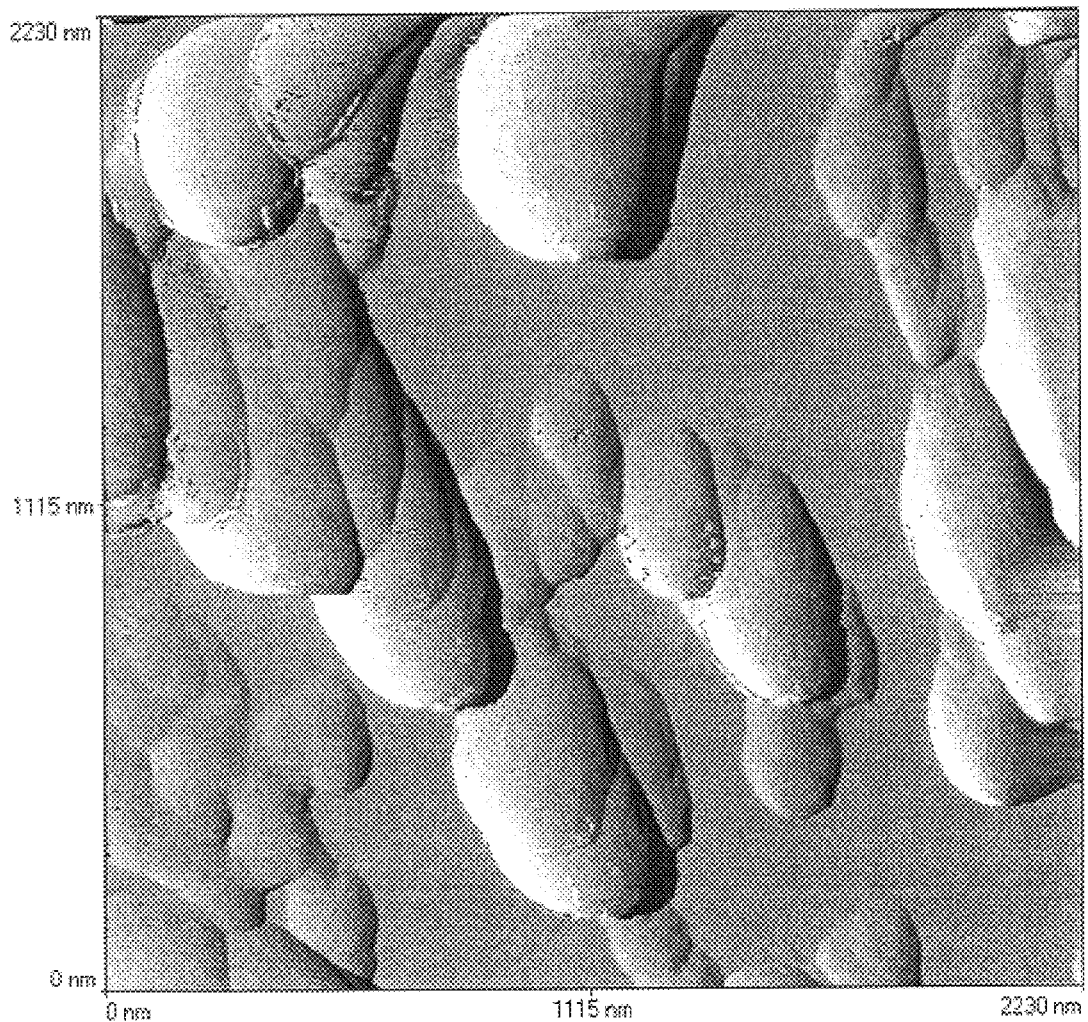
FIG. 1 represents a photograph, taken by atomic force microscopy, of nanoparticles formed from the novel cyclodextrin molecule obtained in Example 2a, namely a mixture of β-cyclodextrins substituted by 6 to 10 fatty acid chains, principally 7, 8 and 9 lauric acid chains.

In the examples, the temperature is given in degrees C. and the pressure is atmospheric pressure unless otherwise indicated.

General points for all examples: Commercial β-cyclodextrin was re-crystallized from water and vacuum dried ($10^{-2}$ Torr) for 2 days at 120° C. or freeze dried. The solvents were pyridine type solvents, for example pyridine, formamide type, for example DMF, sulfoxide type, for example DMSO and furan type, for example THF. These solvents were dried under CaH$_2$ and redistilled before use. The fatty chains were grafted with activated ester type reactants, for example acid chlorides, acid anhydrides, and in particular acid chlorides. The coupling agents were of the diimide type, for example EDCI. The solvents used to form nanoparticles, micelles, liposomes were organic in type, for example acetone and THF.

Part I—Synthesis of Novel Cyclodextrin Entities in Accordance with the Invention

Example 1

(Lauroate)$_y$-β-cyclodextrin

[y = 3 on average with y = 1 to 6]

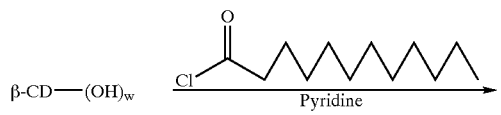

[w = 21]

[x = z = 0; w + y = 21 with y = 1 to 6]

The anhydrous β-cyclodextrin (42.23 g, 1 eq.) was dissolved in freshly distilled pyridine (750 ml, 23° C.) under nitrogen. Lauric acid chloride (34.5 ml, 4 eq.) was added dropwise at ambient temperature and the reaction was left, with stirring, for 24 hours. The solution was poured into water (500 ml, pH=2), The pH was kept at 2 with HCl and the precipitate obtained was filtered and washed with water (500 ml, pH=2). The white powder (65 g) was vacuum dried (10.2 Torr) for 5 hours at 60° C.

The product obtained was a mixture of β-cyclodextrin substituted with 1 to 6 fatty acid chains, principally 2 and 3 lauric acid chains. For this reason, in this example, y is an average of 3 but can vary from 1 to 6.

Example 2

(Lauroate)$_y$-β-cyclodextrin 2.a: (lauroate)$_y$-β-cyclodextrin
[y = 8 on average with y = 6 to 10]

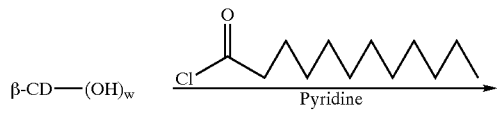

[w = 21]

[x = z = 0; w + y = 21 with y = 6 to 10]

The anhydrous β-cyclodextrin (50.12 g, 1 eq.) was dissolved in freshly distilled pyridine (750 ml, 23° C.) under nitrogen. Lauric acid chloride (93.78 ml, 9 eq.) was added dropwise at ambient temperature and the reaction was left, with stirring, for 24 hours. The solution was poured into water (500 ml, pH=2). The pH was kept at 2 with HCl. The precipitate obtained (0.13 g) was filtered and vacuum dried ($10^{-2}$ Torr) for 5 hours at 60° C.

The product obtained was a mixture of β-cyclodextrin substituted with 6 to 10 fatty acid chains, principally 7, 8 and 9 lauric acid chains.

Silica column chromatography was used to separate the different compounds.

Substitution of the primary alcohols was demonstrated by $^1$H NMR of a compound containing 7 lauric acid chains. The primary alcohol peak OH-6 (δ=4.47 ppm, DMSO-d$^6$) disappeared, the alcohol being substituted by an ester. The secondary alcohols (δ=5.73 ppm (OH-2) and δ=5.67 ppm (OH-3), DMSO-d$^6$) remained unchanged, grafting on the secondary face not occurring or occurring only slightly. The two H-6 hydrogens of the C-6 carbon carrying the primary alcohol OH-6 (δ=3.65 ppm, DMSO-d$^6$) were displaced under the effect of the grafting (δ=4.29–4.21 ppm, DMSO-d$^6$).

2.b: (lauroate)$_y$-β-cyclodextrin
[y = 1 to 21]

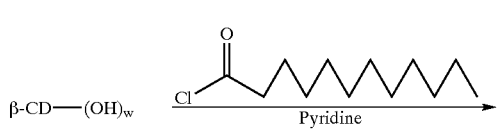

[w = 21]

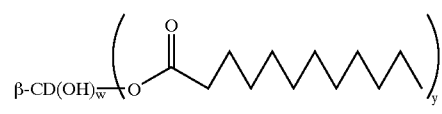

[x = z = 0; w + y = 21 with y = 1 to 21]

The process described in example 2.a was carried out with the following modifications: the lauric acid chloride was added with a number of equivalents of 1 to 25, except between 4 and 9 described in examples 1 and 2a, for 1 equivalent of β-cyclodextrin. The products obtained were a mixture of β-cyclodextrin substituted by 1 to 21 chains of lauric acid depending on the number of equivalents of acid chloride used.

Example 3

(Alkyloate)$_y$-β-cyclodextrin
[y=1 to 21]

3.a: (lauroate)$_y$-β-cyclodextrin
[y = 8 on average with y = 6 to 10]

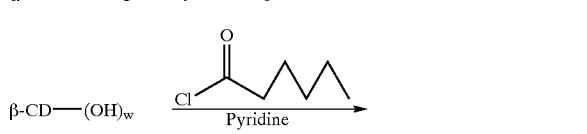

[w = 21]

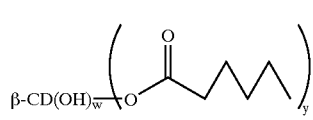

[x = z = 0; w + y = 21 with y = 6 to 10]

The anhydrous β-cyclodextrin (1.71 g, 1 eq.) was dissolved in freshly distilled pyridine (750 ml, 23° C.) under nitrogen. Hexanoic acid chloride (1.97 ml, 9 eq.) was added dropwise at ambient temperature and the reaction was left, with stirring, for 24 hours. The solution was poured into water (100 ml, pH=2). The pH was kept at 2 with HCl and the precipitate obtained was filtered then washed with water (500 ml, pH=2). The white powder (2.1 g) was vacuum dried ($10^{-2}$ Torr) for 5 hours at 60° C.

The product obtained was a mixture of β-cyclodextrin substituted with 6 to 10 fatty acid chains, principally 7, 8 and 9 hexanoic acid chains.

3.b: Chain Length Modification

The preparation was carried out as described in example 3.a but in the presence of a butyric acid chloride (C4), a caprylic acid chloride (C8), a capric acid chloride (C10), a myristic acid chloride (C14), a palmitic acid chloride (C16), a stearic acid chloride (C18) and an arachidic acid chloride (C20).

3.c: Modification of the Number of Equivalents of Acid Chloride Added

The process described in examples 3.a and 3.b was carried out with the following modifications: the acid chloride was added with a number of equivalents of 1 to 25 for 1 equivalent of β-cyclodextrin. The products obtained were a mixture of β cyclodextrin substituted with 1 to 21 fatty acid chains depending on the number of equivalents of the acid chloride used.

Example 4

Heptakis(6-deoxy-6-N,N-dipentylamino)-β-cyclodextrin

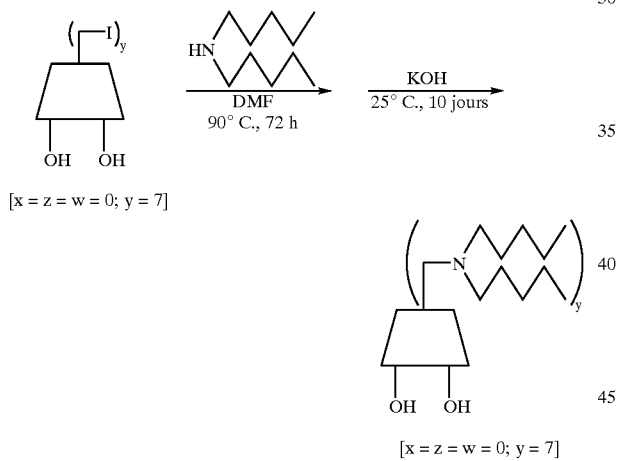

The anhydrous heptakis(6-deoxy-6-iodo)-β-cyclodextrin (Gadelle A and Defaye J, *Angew. Chem.* 103, 94 (1991); H. H. Baer et al. in *Carbohydr. Res.* 228, 307 (1992) (20 g, 1 eq.) was suspended in the N,N-dipentylamine (150.33 ml, 70 eq.) in a nitrogen atmosphere. The mixture was stirred at 90° C. for 15 minutes then 100 ml of anhydrous DMF was slowly added at 90° C. until the product dissolved. The solution was stirred for 72 hours at 90° C. An aqueous KOH solution (30 ml, 30 eq.) was added every 24 hours for 10 days. The solution was cooled to ambient temperature. Water (400 ml) then acetone and an aqueous KOH solution (4 ml) were added. The precipitate obtained was filtered and washed with acetone (7400 ml). The paste obtained was washed with DMF (50 ml, 60° C.) and precipitated by adding water (200 ml), acetone (400 ml) and aqueous KOH solution (2 ml). The white powder was filtered and washed with acetone (200 ml) then vacuum dried ($10^{-2}$ Torr) for 5 hours at 60° C. (12.2 g). The cyclodextrins had amine functions on their primary face defined by the short base of their trapezoidal shape, and secondary alcohol functions on their secondary face defined by the large base of said trapezoid.

Example 5

(Lauroate)$_y$-(4-nitrophenylformate)$_z$-β-cyclodextrin
[y=8 on average with y=6 to 10; z=1 or 2]
Second Graft of Nitro Functional Group ($G_1$):

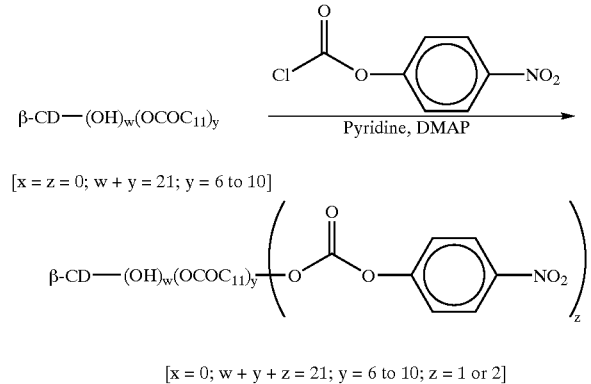

The compound obtained in example 2a (1 g, 1 eq.) was dried and dissolved in anhydrous pyridine (20 ml, 23° C.). 4-nitrophenylchloroformate (0.79 g, 10 eq.) was slowly added with DMAP (0.48 g, 10 eq.) and the mixture was stirred at 23° C. for 24 hours. The solution obtained was poured into water (100 ml, pH=2). The pH was kept at 2 with HCl and the precipitate obtained was filtered and washed with water (500 ml, pH=2). The white powder (2.73 g) was vacuum dried ($10^{-2}$ Torr) for 5 hours at 60° C.

One to two 4-nitrophenylformate groups were grafted onto the compound obtained in example 2a.

Example 6

(Lauroate)$_y$-(ethyloxaloate)$_z$-β-cyclodextrin
[y=8 on average with y=6 to 10; z=1 or 2]
Second Graft of Ester Functional Group ($G_1$):

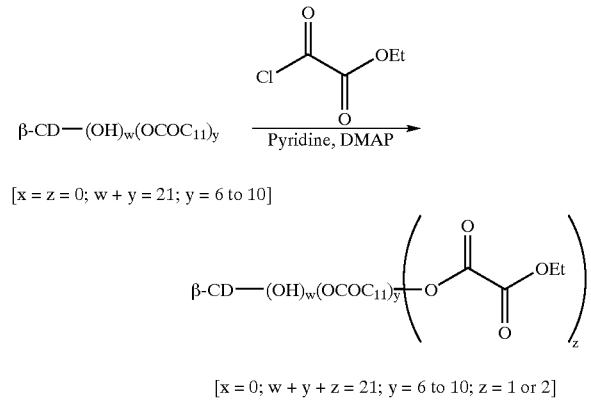

The compound obtained in example 2a (1 g, 1 eq.) was dried and dissolved in anhydrous pyridine (20 ml, 23° C.). Oxalic ethyl chloride (442 µl, 10 eq.) was slowly added with DMAP (0.48 g, 10 eq.) and the mixture was stirred at 23° C. for 24 hours. The solution obtained was poured into water (100 ml, pH=2). The pH was kept to 2 with HCl and the precipitate obtained was filtered and washed with water (500 ml, pH=2). The yellow powder (1.25 g) was vacuum dried ($10^{-2}$ Torr) for 5 hours at 60° C.

One to four ethyl oxalic groups had been grafted onto the compound of example 2a.

Example 7

(Lauroate)$_y$-(chloroethanoate)$_z$-β-cyclodextrin
[y=8 on average with y=6 to 10; z=1 or 2]
Second Graft of Halide Functional group (G$_1$):

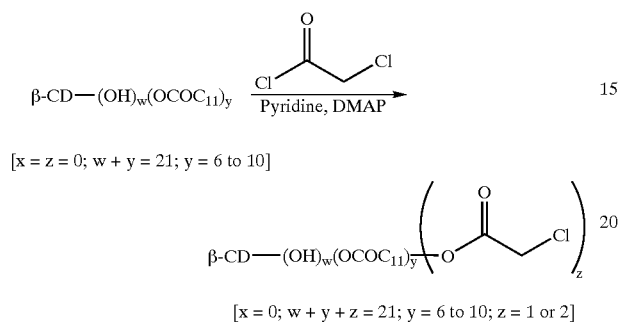

The compound obtained in example 2a (1 g, 1 eq.) was dried and dissolved in anhydrous pyridine (20 ml, 23° C.). Chloroacetyl chloride (316 μl, 10 eq.) was slowly added with the DMAP (0.48 g, 10 eq.) and the mixture was stirred at 23° C. for 24 hours. The solution obtained was poured into water (100 ml, pH=2). Le pH was kept at 2 with HCl and the precipitate obtained was filtered, washed with water (500 ml, pH=2) then recovered from hot acetone. After evaporation, the red paste (0.75 g) obtained was vacuum dried ($10^{-2}$ Torr) for 5 hours at 60° C. One to two chloroacetyl groups had been grafted to the compound of example 2a.

Example 8

(Lauroate)$_y$-(butanedioic monoester)$_z$-β-cyclodextrin
[y=8 on average with y=6 to 10; z=1 or 2]
Second Graft of Acid Functional Group (G$_1$):

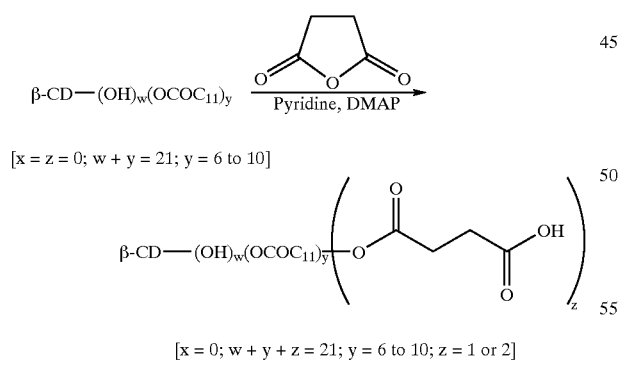

The compound obtained in example 2a (4 g, 1 eq.) was dried and dissolved in anhydrous pyridine (20 ml, 23° C.). Succinic anhydride (0.34 g, 2 eq.) was slowly added with DMAP (0.41 g, 2 eq.) and the mixture was stirred at 23° C. for 24 hours. The solution obtained was poured into water (100 ml, pH=2). The pH was kept to 2 with HCl and the precipitate obtained was filtered and washed with water (500 ml, pH=2). The white powder (3.85 g) was vacuum dried ($10^{-2}$ Torr) for 5 hours at 60° C.

One to two acid groups were grafted to the compound obtained according to example 2a.

Example 9

Heptakis(6-deoxy-6-N,N-dipentylamino)-(butanedioic monoester)$_z$-β-cyclodextrin
[z=1 or 2]
Second Graft of Acid Functional Group (G$_1$)

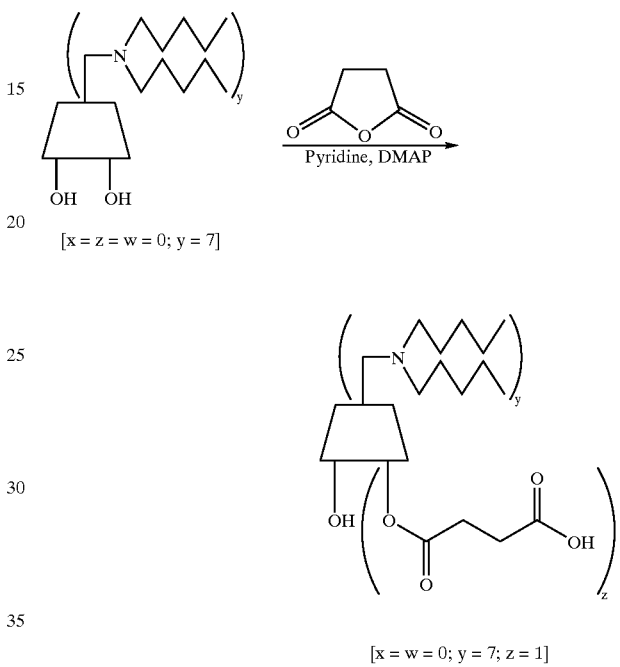

The compound obtained according to example 4 (1 g, 1 eq.) was dried and dissolved in anhydrous pyridine (100 ml, 23° C.). Succinic anhydride (0.057 g, 1.2 eq.) was slowly added with the DMAP (0.58 g, 10 eq.) and the mixture was stirred at 23° C. for 24 hours. The solution obtained was poured into water (100 ml, pH=2). The pH was kept to 2 with HCl and the precipitate obtained was filtered and washed with water (500 ml, pH=2). The white powder (0.75 g) was vacuum dried (10.2 Torr) for 5 hours at 60° C.

One succinic group had been grafted onto the compound of example 4.

Example 10

(Lauroate)$_y$-(oxalic monoester)$_z$-β-cyclodextrin
[y=8 on average with y=6 to 10; z=1 or 2]
Second Graft of Acid Functional Group (G$_1$):

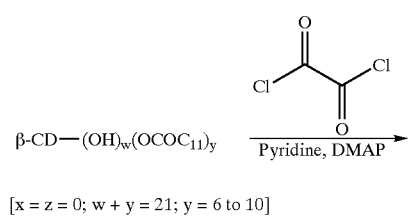

[x = z = 0; w + y = 21; y = 6 to 10]

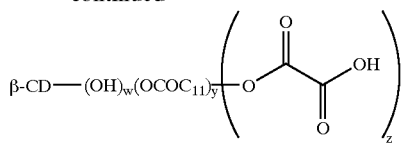

[x = 0; w + y + z = 21; y = 6 to 10; z = 1 or 2]

The compound obtained according to example 2a (1 g, 1 eq.) was dried and dissolved in anhydrous pyridine (20 ml, 23° C.). Oxalic chloride (344 µl, 10 eq.) was slowly added with the DMAP (0.48 g, 10 eq.) and the mixture was stirred at 23° C. for 24 hours. The solution obtained was poured into water (100 ml, pH=2). The pH was kept to 2 with HCl and the precipitate obtained was filtered and washed with water (500 ml, pH=2). The yellow powder (1.25 g) was vacuum dried (10.2 Torr) for 5 hours at 60° C.

One to two acid groups had been grafted to the compound of example 2a.

Example 11

(Lauroate)$_y$-(sulfo)$_z$-β-cyclodextrin
[y=8 on average with y=6 to 10; z=1 or 2]
Second Graft of Acid Sulfonic Functional Group ($G_1$):

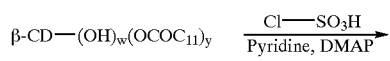

[x = z = 0; w + y = 21; y = 6 to 10]

[x = 0; w + y + z = 21; y = 6 to 10; z = 1 or 2]

The compound obtained in example 2a (1 g, 1 eq.) was dried and dissolved in anhydrous pyridine (20 ml, 23° C.). Chlorosulfonic acid (263 µl, 10 eq.) was slowly added with DMAP (0.48 g, 10 eq.) and the mixture was stirred at 23° C. for 24 hours. The solution obtained was poured into water (100 ml, pH=2). The pH was kept at 2 with HCl and the solution was washed with chloroform (50 ml). The organic phase was dried over MgSO$_4$, filtered and evaporated. The paste obtained (0.70 g) was vacuum dried (10$^{-2}$ Torr) for 5 hours at 60° C.

One to two sulfonic groups had been grafted onto the compound of example 2a.

Example 12

(Lauroate)$_y$-(oxaloate de N-(2-aminoethyl)amide)$_z$-β-cyclodextrin
[y=8 on average with y=6 to 10; z=1]
Second Graft of Amine Functional Group ($G_1$):

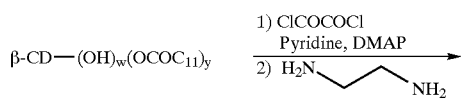

[x = z = 0; w + y = 21; y = 6 to 10]

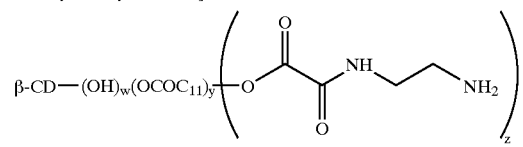

[x = 0; w + y + z = 21; y = 6 to 10; z = 1]

The compound obtained in example 2a (1 g, 1 eq.) was dried and dissolved in anhydrous pyridine (20 ml, 23° C.). Oxalic chloride (344 µl, 10 eq.) was slowly added with the DMAP (0.48 g, 10 eq.) and the mixture was stirred at 23° C. for 24 hours. Then ethylene diamine (233 µl, 10 eq.) was added. The solution obtained was poured into water (100 ml, pH=7). The precipitate obtained was filtered and washed with water (500 ml, pH=2). The yellow powder (0.75 g) was vacuum dried (10$^{-2}$ Torr) for 5 hours at 60° C.

One ethylene diamine group had been grafted onto the compound of example 2a.

Starting from the compounds obtained in examples 8, 10 and 12, it was easy to graft specific groups $G_2$, for example sugars, polyols, oligosaccharides, polysaccharides, amino acids, peptides, proteins, nucleotides, nucleosides, oligonucleotides, oligonucleosides, chromophores, polymers, steroids, vitamins and other bioactive molecules.

Example 13

(Lauroate)$_y$-((N-(2-aminoethyl)lactonamide succinamido)$_z$-β-cyclodextrin. (Third Graft)
[y=8 on average with y=6 to 10; z=1]

[y = 8 on average with y = 6 to 10; z = 1]

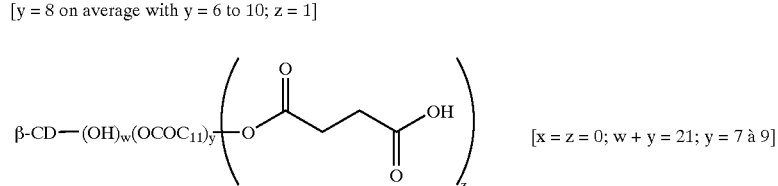

[x = z = 0; w + y = 21; y = 7 à 9]

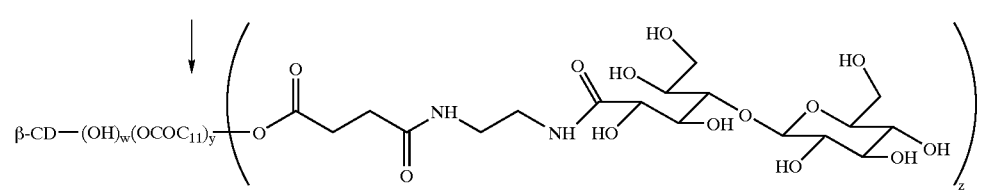

[x = 0; w + y + z = 21; y = 7 à 9; z = 1]

The compound obtained in example 8 (0.17 g, 1 eq.) was dried and dissolved in anhydrous DMSO (80 ml, 23° C.). N-(2-aminoethyl)lactonamide (Scholnick, F. et al., J. Dairy Science, 63(3), 471–473 (1980); Otada, Kazuya et al., Biochim. Biophys. Acta, 1112(1), 1–6 (1992); Otada, Kazuya et al., Biochim. Biophys. Acta, 1145(1), 33–41 (1993) and Ouchi, Tatsuro, et al., ACS Symp. Ser., 680 (poly(ethyleneglycol)), 284–296 (1997) (0.24 g, 10 eq.) was slowly added and the mixture was stirred at 60° C. for 72 hours in the presence of EDCI (0.16 g, 10 eq.).

The reaction was poured into water (100 ml, pH=7). The precipitate obtained was filtered and washed with water (500 ml, pH=2). The white powder (0.1 g) was vacuum dried ($10^{-2}$ Torr) for 5 hours at 60° C.

A lactomide group grafted to the compound obtained in example 8 was obtained.

Example 14

Heptakis(6-deoxy-6-N,Ndipentylamino)-((N-(2-aminoethyl)lactonamide succinamido)$_z$-β-cyclodextrin (Third Graft)

[z = 1]

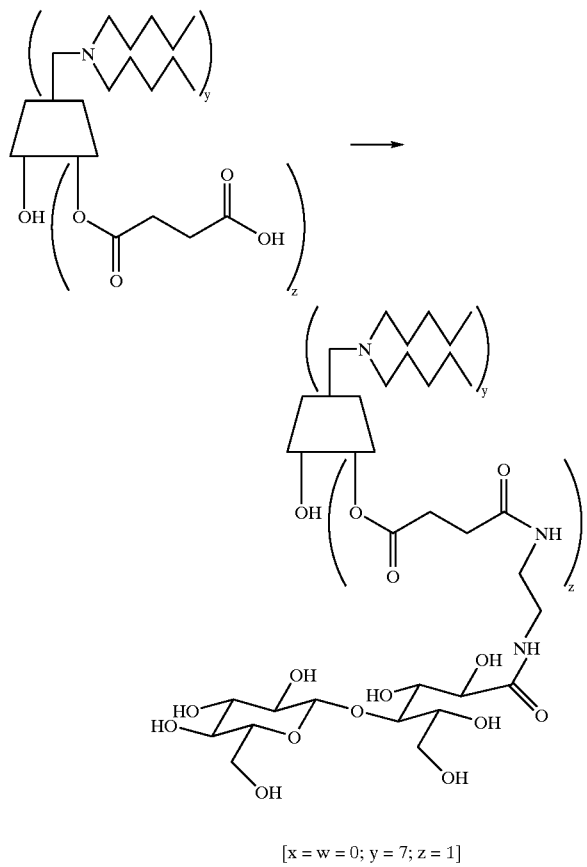

[x = w = 0; y = 7; z = 1]

The compound obtained in example 9 (0.75 g, 1 eq.) was dried and dissolved in anhydrous DMSO (80 ml, 23° C.). N-(2-aminoethyl)lactonamide (1.36 g, 10 eq.) was slowly added and the mixture was stirred at 60° C. for 72 hours in the presence of EDCI (0.65 g, 10 eq.).

The reaction was poured into water (100 ml, pH=7). The precipitate obtained was filtered and washed with water (500 ml, pH=2). The white powder (0.5 g) was vacuum dried ($10^{-2}$ Torr) for 5 hours at 60° C.

A lactomide group grafted onto the compound obtained in example 8 was obtained.

Part II—Nanoparticle Formation

Example 15

15a: Nanoparticle Formation from Compound Obtained in Example 2a 300 mg of the compound prepared in example 2a was dissolved in acetone (150 ml) with stirring. The solution was then added at a constant rate (1 ml/s) to distilled water (450 ml) with stirring to form a milky solution. The acetone was then evaporated off using a rotary evaporator at 25° C. and water was added to the solution obtained to provide a concentration of 0.5 mg/ml.

The average size of the nanoparticles was measured by light diffusion. The analyses were made using a 4700C spectrometer constructed around Malvern instruments (Malvern, U.K.) with a 40 mW Siemens laser.

One milliliter of the aqueous 0.5 mg/ml nanoparticle solution was placed in a tube and placed in the cell of the apparatus. The temperature was fixed at 25° C. The angle of the photomuliplier was fixed at the standard value of 90° to study all of the particle sizes while concentrating more on sizes of the order of 100 to 600 nm. The analysis was made in Automatic mode.

The average nanoparticle size, measured by light diffusion, was 212 nm±5 nm.

The nanoparticle stability was studied at 3° C., 23° C. and 40° C. by visual observation; the size was measured by light diffusion and atomic force microscopic observation:

The support was composed of a 17 mm diameter steel roundel onto which was fixed a 1 $cm^2$ muscovite mica plate using adhesive tape. As the mica was constituted by a plurality of layers, one layer was removed to obtain a very flat support with a minimum of defects. Five μl of the 0.5 mg/ml nanoparticle solution was deposited on the mica and placed in an oven at 40° C. for 10 minutes to evaporate off the water. This step was repeated to deposit a total of 20 μl. Finally, the deposit was placed in a desiccator for 24 h to dry it.

The nanoparticles were viewed in Contact and Non-Contact modes. With the nanoparticles in support gels, Contact mode was used.

The cantilever used was an LRF type resonating at a frequency of 150 kHz in Non-Contact mode. The Scan Rate was fixed at 1.5 Hz in Contact mode and 0.5 Hz in Non-Contact mode.

The results shown in the accompanying FIG. 1 show that the nanoparticles were perfectly stable over a study period of at least 20 months at the three temperatures studied.

15.b: Formation of Nanoparticles from the Compounds Obtained in Examples 1 to 3 and 5 to 13

The nanoparticles were obtained using the protocol described in example 15a from the compounds obtained in examples 1 to 3 and 5 to 13. They were perfectly stable over a study period of at least 20 months at the three temperatures studied.

15.c 300 mg of the compound prepared in examples 1 to 3 and 5 to 13 was dissolved in acetone (150 ml) with stirring. The solution was then added at a constant rate (1 ml/s ) to distilled water (450 ml) with stirring to form a milky solution. The acetone was then evaporated off using a rotary evaporator at 25° C. and water was added to the solution obtained to provide a concentration of 0.5 mg/ml. 3 g of soya phospholipids (phosphatidylcholine, 90% pure) were then added to the solution. After completely dissolving (about 5 hours at ambient temperature) under moderate magnetic stirring, liposomes were formed by stirring the solution at a high shear rate (Ultraturrax, 15000 rpm) for about 30 minutes.

Transmission electron microscopic analysis identified liposomes with a size in the range 50 to 800 nm.

The stability of the nanoparticles was studied at 3° C., 23° C. and 40° C.; it was excellent.

Example 16

Formation of Nanoparticles from Compounds Obtained in Examples 4 and 14

16.a 300 mg of the compound prepared in example 4 was dissolved in THF (12 ml) with stirring. The solution was then added at a constant rate (1 ml/s) to distilled water (588 ml) with stirring to form a milky solution. The THF was then evaporated off using a rotary evaporator at 25° C. and water was added to the solution obtained to provide a concentration of 0.5 mg/ml.

Light diffusion analysis identified two populations with different sizes: one at 154 nm±20 nm and the other at 523 nm±100 nm.

Figure 2:
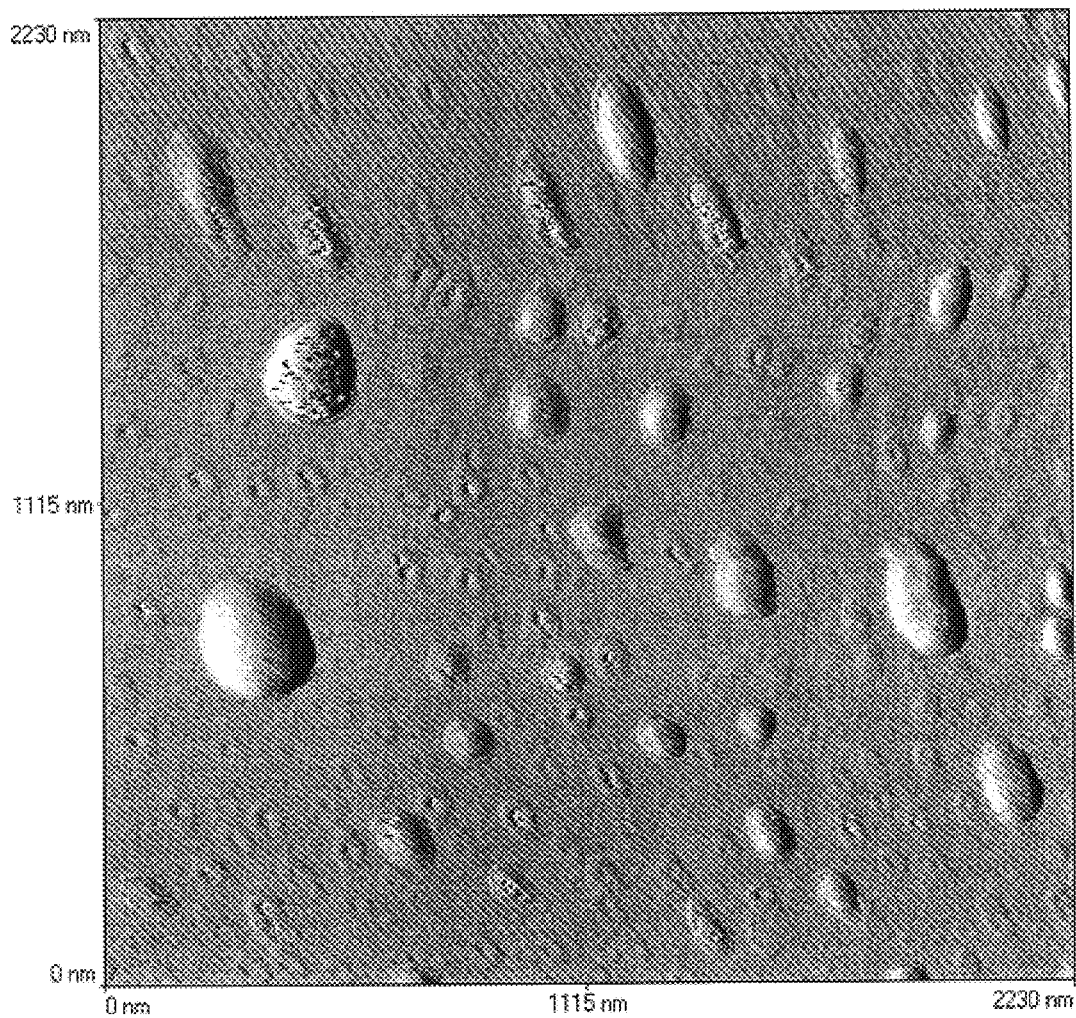
FIG. 2 represents a view similar to that of FIG. 1 of nanoparticles obtained from the compound of Example 4, namely heptakis(6-deoxy-6iodo)-β-cyclodextrin substituted by a plurality of groups derived from N,N-dipentylamine.
Figure 3:
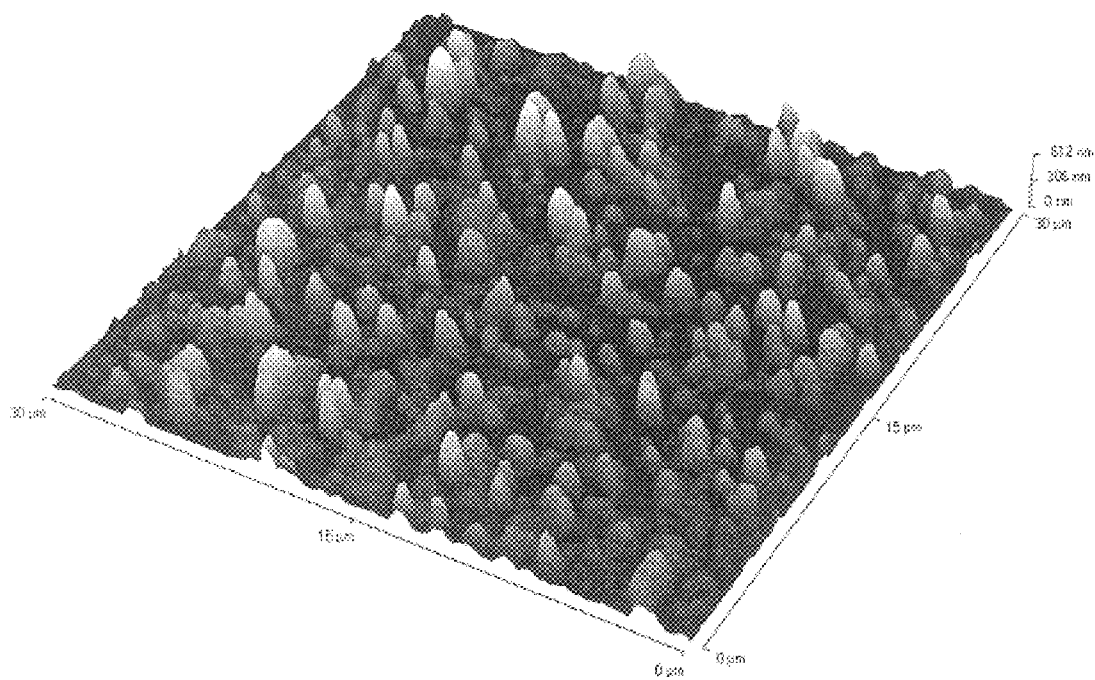
FIG. 3 represents a three-dimensional view by atomic force microscopy of nanoparticles in a carbomer gel after 18 days at 23° C., these nanoparticles being obtained from the novel chemical cyclodextrin entity obtained in example 24, namely (lauroate)$_y$-β-cyclodextrin [y=8 on average with y=6 to 10].

The nanoparticle stability was studied at 3° C., 23° C. and 40° C. by visual observation, the size was measured by light diffusion and atomic force microscopic observation (FIG. 2). The results showed that the nanoparticles were stable over a period of 25 days at 3° C., 200 days at 23° C. and 250 days at 40° C.

16.b: Formation of Nanoparticles from Compounds Obtained from Example 14

The nanoparticles were produced using the protocol of example 16a from the compound obtained in example 14. The nanoparticles were stable over a period of 25 days at 3° C., 200 days at 23° C. and 250 days at 40° C.

16.c 300 mg of the compound prepared in examples 4 or 14 was dissolved in THF (12 ml) with stirring. The solution was then added at a constant rate (1 ml/s) to distilled water (588 ml) with stirring to form a milky solution. The THF was then evaporated off using a rotary evaporator at 25° C. and water was added to the solution obtained to provide a concentration of 0.5 mg/ml. 3 g of soya phospholipids (phosphatidylcholine, 90% pure) were then added to the solution. After completely dissolving (about 5 hours at ambient temperature) under moderate magnetic stirring, liposomes were formed by stirring the solution at a high shear rate (Ultraturrax, 15000 rpm) for about 30 minutes.

Transmission electron microscopic analysis identified liposomes with a size in the range 50 to 800 nm.

The stability of the nanoparticles was studied at 3° C., 23° C. and 40° C.; it was excellent.

Example 17

Commercial β-cyclodextrin

The procedure of example 15 was followed but instead of using the compound obtained in example 2, a commercial β-cyclodextrin with an identical molar concentration was used.

The solution obtained was translucent as β-cyclodextrin is soluble in water and no nanoparticles are formed.

Example 18

18.a

The method described examples 15 and 16 was carried out with the following modifications: the aqueous phase was added to the organic phase.

The nanoparticles obtained had the same characteristics as in examples 15 and 16.

18.b

The method described examples 15 and 16 was carried out with the following modifications: the aqueous phase originally containing 5 g of soya phospholipids (phosphatidylcholine, 90% pure) was added to the organic phase after completely dissolving the phospholipids.

After evaporating off the organic phase, liposomes were formed by stirring the solution at a very high shear rate (Ultraturrax, 15000 rpm) for about 30 minutes.

Transmission electron microscopic analysis identified liposomes with a size in the range 50 to 800 nm.

The stability of the nanoparticles was studied at 3° C., 23° C. and 40° C.; it was excellent.

Example 19

Modification of Nanoparticle Size

Nanoparticle size is a function of the different parameters of flow rate, stirring and temperature. The method described in example 18 was followed, adjusting the rate of adding the aqueous phase to the organic phase. For a rate of 20 ml/s, the nanoparticle size was only 125 nm±5 nm.

The nanoparticles obtained had the same stability as those of example 18.

Example 20

20.a

The procedure of example 15a was followed, but the quantity of product from example 2a added was 3 g, giving a final concentration of 0.5% of substituted β-cyclodextrins i.e., 0.00193 mole/l of substituted β-cyclodextrins.

The milky solution became opaque and very white with the nanoparticles formed which were very stable.

20.b

The procedure of example 20a was followed but a quantity of phospholipids in the range 0.1% to 10% (w/w) was added. After completely dissolving (5 hours at about ambient temperature) with moderate magnetic stirring, liposomes were formed by stirring the solution at a high shear rate (Ultraturrax, 15000 rpm) for about 30 minutes.

Transmission electron microscopic analysis identified liposomes with a size in the range 50 to 800 nm.

The stability of the nanoparticles was studied at 3° C., 23° C. and 40° C.; it was excellent.

Example 21

21.a

The method described in example 15a was followed with the following modifications: 300 mg of the compound prepared in example 2a and 300 mg of sorbitan trioleate were dissolved in acetone (150 ml), with magnetic stirring.

The average size of the nanoparticles, measured by light diffusion, was 190 nm±5 nm.

21.b

The method described in example 15c was carried out with the following modifications: 300 mg of the compound prepared in example 2a and 300 mg of sorbitan trioleate were dissolved in acetone (150 ml), with stirring, and 3 g of soya phospholipids (phosphatidylcholine, 90% pure) were added to the aqueous phase. After completely dissolving (5 hours at about ambient temperature) with moderate magnetic stirring, liposomes were formed by stirring the solution at a high shear rate (Ultraturrax, 15000 rpm) for about 30 minutes.

Transmission electron microscopic analysis identified liposomes with a size in the range 50 to 800 nm.

The stability of the nanoparticles was studied at 3° C., 23° C. and 40° C.; it was excellent.

Example 22

22.a

The method described in example 15a was carried out with the following modifications: 300 mg of puronic acid was dissolved in water (450 ml), with magnetic stirring.

The average size of the nanoparticles, measured by light diffusion, was 190 nm ±15 nm.

22.b

The method described in example 15c was carried out with the following modifications: 300 mg of puronic acid and 3 g of soya phospholipids (phosphatidylcholine, 90% pure) were dissolved in water (450 ml), with magnetic stirring.

After completely dissolving (5 hours at about ambient temperature) with moderate magnetic stirring, liposomes were formed by stirring the solution at a high shear rate (Ultraturrax, 15000 rpm) for about 30 minutes.

Transmission electron microscopic analysis identified liposomes with a size 50 to 800 nm.

The stability of the nanoparticles was studied at 3° C., 23° C. and 40° C.; it was excellent.

Example 23

The method described in example 16 was carried out with the following modifications: 300 mg of the compound prepared in example 4 and 300 mg of sorbitan trioleate were dissolved in THF (12 ml), with magnetic stirring.

The average size of the nanoparticles, measured by light diffusion, was 190 nm±5 nm.

Example 24

The nanoparticles prepared in example 15a (5 ml) were added to a gel support (carbomer) (10 g, 0.5%) and the mixture was homogenized.

The stability of the nanoparticles was studied at 23° C. and 40° C. by visual observation and by atomic force microscopy. The results shows that the nanoparticles were stable over a study period of 6 months at 23° C. and at 40° C. Atomic force microscopic analysis showed the presence of nanoparticles of 180 nm±20 nm in the gels after 50 days at 23° C. and at 40° C.

Example 25

1. Preparation of Nanoparticles in the Presence of a Hydrosoluble Active Ingredient 25.a The procedure of example 20a was followed, but 6 g of caffeine was added to the aqueous phase. The average size of the nanoparticles obtained was 224 nm±13 nm.

25-b

The procedure of example 20a was followed, but 6 g of caffeine was added to the aqueous phase and the organic phase was constituted by 1.3 g of commercial β-cyclodextrin in acetone at the same molar concentration as the substituted β-cyclodextrin (0.00193 M).

The solution was clear and translucent as no nanoparticles were present. Stability of samples obtained in 25-a and 25-b:

| Time | Day 0 | 20 days | 30 days | 2.5 months |
|---|---|---|---|---|
| 25a-20° C. | Whitish suspension | Whitish suspension | Whitish suspension | Whitish suspension with slight precipitate |
| 25a-45° C. | Whitish suspension | Whitish suspension | Whitish suspension | Whitish suspension |
| 25b-20° C. | Translucent solution | Translucent solution | Translucent solution | Translucent solution |
| 25b-45° C. | Translucent solution | Translucent solution | Translucent solution | Translucent solution |

The nanoparticles obtained with the caffeine (sample 25a) were stable over time at 20° C. and at 45° C.

2. Activity Tests

Cutaneous Penetration Test

Cutaneous penetration tests were carried out on the products from examples 25a and 25b, compared with a sample of liposomed caffeine and free caffeine. The caffeine concentration was identical in the 4 products tested.

The above products were deposited (2 g) onto the skin of male hairless rats mounted on a 2.54 cm² Franz cell.

The receptor chamber was constituted by a PBS buffer and antibiotics. Diffusion was monitored over time by sampling from the receptor chamber and analysis by high performance liquid chromatography.

The table below summarizes the results obtained, namely the average quantities of caffeine per unit surface ($\mu g/cm^2$), which had diffused into the receptor chamber after 24 hours:

| Time (hours) | Caffeine free | Caffeine liposomed | β-Cyclodextrins example 25-a | β-Cyclodextrins example 25-b |
|---|---|---|---|---|
| 0 | 0 | 0 | 0 | 0 |
| 24 | 1783 | 593 | 568 | 235 |

After rinsing the biopsy used in the diffusion study, it was kept in the Franz cell for 24 hours without donors.

The quantity of active ingredient liberated in the PBS buffer was then analyzed by HPLC, to study the ability of the skin to temporarily retain the test solution (Release study).

After the release study, the Franz cell was dismantled and the biopsy was brought into contact with an ethanolic solution for 24 hours to quantify the caffeine still present in the skin and to demonstrate the capacity of the skin to store the active ingredient (storage)

| $\mu g/cm2$ | Caffeine free | Caffeine liposomed | β-Cyclodextrins example 25-a | β-Cyclodextrins example 25-b |
|---|---|---|---|---|
| Release | 286.8 ± 28.36 | 261.03 ± 48.55 | 224.37 ± 28.64 | 137.57 ± 28.74 |
| Storage | 26.57 ± 6.55 | 22.2 ± 2.47 | 19.1 ± 4.32 | 10.67 ± 5.45 |

The diffusion results show that the product from example 25-a (nanoparticles formed with substituted β-cyclodextrins) enabled at least the same diffusion of the active ingredient as the diffusion observed with liposomes which is the vector of choice for active ingredient penetration. In contrast, the results obtained with the product from example 25-b (commercial β-cyclodextrin) show no diffusion of the active ingredient through the skin. The release studies and storage studies confirm that the product from example 25-a is an effective vector for active ingredient in skin.

Example 26

1. Preparation of Nanoparticles in the Presence of a Liposoluble Active Ingredient 26-a The procedure of example 20a was followed but 0.6 g of vitamin E was added to the acetone, namely a final concentration of 0.1% of vitamin E. The average size of the nanoparticles was 252 nm±12 nm.

26-b

The method of example 20a was followed, but 0.6 g of vitamin E was added to the organic phase constituted by acetone and commercial β-cyclodextrin at the same molar concentration as the substituted β-cyclodextrin (0.00191 M) (example 26-a).

The solution was clear and transparent due to the absence of nanoparticles.

26-c

Liposomes were produced with 0.1% of vitamin E with 3% of soya licithin.

26-d

A reference was produced constituted by 0.1% of vitamin E in a water+acetone mixture.

A stability study of products 26-a and 26-b was carried out:

| Time | Day 0 | 7 days | 20 days | 2 months |
|---|---|---|---|---|
| 26-a-20° C. | Whitish suspension | Whitish suspension | Whitish suspension | Whitish suspension with slight precipitate |
| 26-a-45° C. | Whitish suspension | Whitish suspension | Whitish suspension | Whitish suspension |
| 26-b-20° C. | Translucent solution | Translucent solution with VitE on surface | Translucent solution with VitE on surface | Translucent solution with VitE on surface (+) |
| 26-b-45° C. | Translucent solution | Translucent solution VitE on surface | Translucent solution VitE on surface | Translucent solution VitE on surface (++) |

The stability of sample 26-a at 20° C. and 45° C. over a period of 2 months was good: the nanoparticles were stable, in contrast to sample 26-b where the active ingredient appeared on the surface due to the absence of nanoparticles.

The vitamin E content was determined by HPLC (fluorescence) and evaluated for each sample:

| | Vitamin E determination |
|---|---|
| 26-a | 0.0881% |
| 26-b | 0.0246% |
| 26-c | 0.0182% |
| 26-d | 0.0943% |

The vitamin E determination carried out on the 4 samples demonstrated that the substituted β-cyclodextrins of example 2a encapsulated the vitamin E highly effectively: 0.0881% could be measured in the whitish suspension for 0.1% of vitamin E used.

Sample B constituted by the commercial β-cyclodextrin only had 0.0246% of vitamin E in the suspension obtained, explained by the fact that the vitamin E was on the surface.

Sample C constituted by the liposome did not effectively encapsulate the vitamin E and solution D constituted by the reference confirmed the vitamin E determination.

2. Activity Tests

Cutaneous Penetration Study

Cutaneous penetration studies were carried out on products 26-a, 26-b, 26-c and 26-d from example 26. These products were deposited (2 g) onto the skin of male hairless rates mounted on a 2.54 $cm^2$ Franz cell.

The receptor chamber was constituted by ethoxydiglycol and antibiotics. Diffusion was monitored over time by sampling from the receptor chamber then HPLC analysis (fluorescence).

The table below summarizes the results for the percentage of vitamin E diffused after 48 hours:

| Time (hours) | Vit E free | Vit E liposomed | β-Cyclodextrins example 26-a | β-Cyclodextrins example 26-b |
|---|---|---|---|---|
| 0 | 0 | 0 | 0 | 0 |
| 48 | 10.32% | 2.04% | 5.8% | 1.52% |

After rinsing the biopsy used in the diffusion study, it was kept in the Franz cell for 24 hours without donors.

The quantity of active ingredient liberated in the ethoxydiglycol was then analyzed by HPLC, underlining the ability of the skin to temporarily retain the test solution (release study).

After the release study, the Franz cell was dismantled and the biopsy was brought into contact with an ethanolic solution for 24 hours to quantify the vitamin E still present in the skin and to demonstrate the capacity of the skin to retain the active ingredient over a prolonged period.

| % diffusion | Vit E free | Vit E liposomed | β-Cyclodextrins example 26a | β-Cyclodextrins example 26-b |
|---|---|---|---|---|
| Release | 3.33 ± 0.9 | 0.21 ± 0.14 | 1.46 ± 0.16 | 1.47 ± 0.7 |
| Storage | 1.74 ± 0.24 | 0.66 ± 0.21 | 2.81 ± 0.57 | 1.1 ± 0.09 |

The diffusion results show that the product from example 26-a (nanoparticles formed with substituted β-cyclodextrins) enabled the active ingredient to diffuse more than the diffusion observed with liposomes, in contrast to the product from example 26-b (commercial β-cyclodextrin) which did not allow good diffusion of the vitamin E through the skin.

The release studies and storage studies confirm that the product from example 26-a is an effective vector for active ingredients in skin.

Example 27

Use of the products of the invention in cosmetic formulations or pharmaceutical formulations of the oil-in-water type.

Formulation 27a

| A | Water | qsp 100 |
|---|---|---|
|   | Butylene Glycol | 2 |
|   | Glycerin | 3 |
|   | Sodium Dihydroxycetyl Phosphate, Isopropyl Hydroxycetyl Ether | 2 |
| B | Glycol Stearate SE | 14 |
|   | Triisononanoin | 5 |
|   | Octyl Cocoate | 6 |
| C | Butylene Glycol, Methylparaben, Ethylparaben, Propylparaben, pH adjusted to 5.5 | 2 |
| D | Products of the invention | 0.01–10% |

Phases A and B were heated separately to 75° C. then B was added to A with vigorous stirring: C then D are then added while the cream which was formed was cooled.

Formulation 27b

| A | Water | qsp 100 |
|---|---|---|
|   | Butylene Glycol | 2 |
|   | Glycerin | 3 |
|   | Polyacrylamide, Isoparaffin, Laureth-7 | 2.8 |
| B | Butylene Glycol, Methylparaben, Ethylparaben, Propylparaben; | 2 |
|   | Phenoxyethanol, Methylparaben, Propylparaben, Butylparaben, Ethylparaben | 2 |
|   | Butylene Glycol | 0.5 |
| C | Products of the invention | 0.01–10% |

Phase A was heated to 75° C.; B then C were added with stirring while the formula thus formed was cooled.

Formulation 27c

| A | Carbomer | 0.50 |
|---|---|---|
|   | Propylene Glycol | 3 |
|   | Glycerol | 5 |
|   | Water | qsp 100 |
| B | Octyl Cocoate | 5 |
|   | Bisabolol | 0.30 |
|   | Dimethicone | 0.30 |
| C | Sodium Hydroxide | 1.60 |
| D | Phenoxyethanol, Methylparaben, Propylparaben, Butylparaben, Ethylparaben | 0.50 |
| E | Fragrance | 0.30 |
| F | Products of the invention | 0.01–10% |

Phases A and B were heated separately to 75° C. then B was added to A with vigorous stirring: C then D then E then F were then added while the cream which was formed was cooled.

Example 28

In Accordance with the Invention
Use of the Products of the Invention in a Water-in-oil Type Formulation

| A | PEG 30-dipolyhydroxystearate | 3 |
|---|---|---|
|   | Capric triglycerides | 3 |
|   | Cetearyl Octanoate | 4 |
|   | Dibutyl Adipate | 3 |
|   | Grape seed oil | 1.5 |
|   | Jojoba oil | 1.5 |
|   | Phenoxyethanol, Methylparaben, Propylparaben, Butylparaben, Ethylparaben | 0.5 |
| B | Glycerin | 3 |
|   | Butylene Glycol | 3 |
|   | Magnesium Sulfate | 0.5 |
|   | EDTA | 0.05 |
|   | Water | qsp 100 |
| C | Cyclomethicone | 1 |
|   | Dimethicone | 1 |
| D | Fragrance | 0.3 |
| E | Products of the invention | 0.01–10% |

Phases A and B were heated separately to 75° C. then B was added to A with vigorous stirring: C then D then E then F were then added while the cream which was formed was cooled.

Example 29

In Accordance with the Invention
Use of Products of the Invention in a Shampoo or Shower Gel Type Formulation

| A | Xanthan gum | 0.8 |
|---|---|---|
|   | Water | qsp 100 |
| B | Butylene Glycol, Methylparaben, Ethylparaben, Propylparaben | 0.5 |
|   | Phenoxyethanol, Methylparaben, Propylparaben, Butylparaben, Ethylparaben | 0.5 |
| C | Citric acid | 0.8 |
| D | Sodium Laureth Sulfate | 40.0 |
| E | Product of the invention | 0.01–10% |

Phases A and B were prepared separately at ambient temperature, then B was added to A with stirring; C then D then E were then added with moderate stirring.

Example 30

In Accordance with the Invention
Use of the Products of the Invention in a Lipstick Type Formulation and in Other Anhydrous Products

| A | Mineral wax | 17.0 |
|---|---|---|
|   | Isostearyl Isostearate | 31.5 |
|   | Propylene Glycol Dipelargonate | 2.6 |
|   | Propylene Glycol Isostearate | 1.7 |
|   | Beeswax/PEG 8 | 3.0 |
|   | Hydrogenated palm kernel oil | 3.4 |
|   | Hydrogenated palm glyceride oil |   |
|   | Lanolin oil | 3.4 |
|   | Sesame seed oil | 1.7 |
|   | Cetyl Lactate | 1.7 |
|   | Mineral oil, lanolinic alcohol | 3.0 |

-continued

| B | Castor oil | qsp 100 |
| | Titanium dioxide | 3.9 |
| | Mixture of organic and/or mineral pigments | 3 |
| C | Products of the invention | 0.01–5% |

Phases A and B were heated separately to 80° C. then B was added to A with stirring: C was then added after obtaining a homogeneous mixture of A/B, at a temperature in the range 20° C. to 80° C.

Example 31

In Accordance with the Invention
Use of Products of the Invention in an Aqueous Gel Formulation (Eye Liners, Thinners, etc.)

| A | Water | qsp 100 |
| | Carboxyvinyl polymer (also termed carbomer) | 0.5 |
| | Butylene Glycol | 15 |
| | Phenoxyethanol, Methylparaben, Propylparaben, Butylparaben, Ethylparaben | 0.5 |
| B | Products of the invention | 0.01–10% |

Phase A was prepared by adding all the ingredients and heating to 80° C. to obtain a homogeneous mixture. B was then added to A with vigorous stirring while the gel thus formed was cooled.

Example 32

Innocuity Tests
Evaluation of the Cosmetic Acceptability of a Preparation Containing the Products of the Invention Toxicological tests were carried out on the compound obtained in example 2a incorporated in an amount of 10% into a 0.5% xanthan gel, by ocular evaluation in the rabbit, by a study of the absence of abnormal toxicity by a single oral administration to the rat and by a sensitization power study in the guinea-pig.

At the same time, a toxicological study was carried out under the same experimental conditions on commercial β-cyclodextrin incorporated in an amount of 10% into a 0.5% xanthan gel.

1. Evaluation of Primary Dermal Irritation in the Rabbit
The preparations described above were applied undiluted in a dose of 0.5 ml to the skin of 3 rabbits using the method recommended by the OECD directive regarding the study of "The acute dermal irritant/corrosive effect".

The products were classified in accordance with the criteria in the order of Feb. 1, 1982 published in the JORF [Official journal of the French Republic] on Feb. 2, 1982.

The results of these tests allowed the conclusion to be drawn that the preparation containing commercial β-cyclodextrin had been classed as being a slight irritant for the skin while the preparation containing the compound obtained in example 2a (β-cyclodextrin substituted by lauric acid chains) was classed as non irritant to the skin.

Substitution of the β-cyclodextrin thus reduced the irritant nature of cyclodextrins.

2. Evaluation of Ocular Irritation in the Rabbit
The preparations described above were instilled pure all at once in an amount of 0.1 ml into the eye of three rabbits using the method recommended by OECD directive n° 405 dated Feb. 24, 1987 regarding the study of the "acute ocular irritant/corrosive effect"

The results of this test enabled the conclusion to be drawn that the preparations could be considered to be non irritant for the eyes, within the meaning of EEC directive 91/326, used pure or without dilution.

3. Test of Absence of Abnormal Toxicity By Single Oral Administration to the Rat
The preparations described above were orally administered all at once in a dose of 5 g/kg of body weight to 5 male rats and 5 female rats using the protocol inspired by OECD directive n° 401 dated Feb. 24, 1987 and adapted for cosmetic products.

The DL0 and DL50 were found to be higher than 5000 mg/kg. The test preparations were thus not classified as being among those which are dangerous by ingestion.

4. Evaluation of Potential Cutaneous Sensitization in the Guinea-pig
The preparations described above were subjected to the maximization test described by Magnusson and Kligmann, which protocol was in accordance with OECD directive n°406.

The preparations were classified as non sensitizing by contact with the skin.

What is claimed is:

1. A method of cosmetic care comprising topically delivering on skin zones to which said cosmetic care is sought at least one substituted cyclodextrin in the form of at least one nanoparticle or at least one micelle having the following chemical formula:

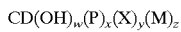

where:
CD represents a structure based on a non-hydroxyalkylated cyclodextrin without its hydroxyl groups, the cyclodextrin comprising one or more of α-cyclodextrin, β-cyclodextrin or γ-cyclodextrin,
OH represents the free hydroxyl groups of the cyclodextrin,
w, x, y, and z are defined such that:
when the cyclodextrin is an α-cyclodextrin, x and z are each independently a whole number between 0 and 17, y is a whole number between 1 and 18, and w represents a whole number such that a sum of w+x+y+z is 18,
when the cyclodextrin is a β-cyclodextrin, x and z are each independently a whole number between 0 and 20, y is a whole number between 1 and 21, and w represents a whole number such that a sum of w+x+y+z is 21,
when the cyclodextrin is a γ-cyclodextrin, x and z are each independently a whole number between 0 and 23, y is a whole number between 1 and 24, and w represents a whole number such that a sum of w+x+y+z is 24,
X represents a substituent having a formula —O—C(=O)—R or —N($R_1R_2$) defined below, replacing the —OH portion of at least one primary alcohol function and optionally at least one secondary alcohol function;
P represents a radical substituting a primary or secondary hydroxyl group selected from the group consisting of a phosphate, an ose and an oside, when at least one X represents O—C(=O)—R;
P represents a radical substituting a primary or secondary hydroxyl group selected rom the group consisting of a sulfate, a phosphate, an ose and an oside, when at least one X represents —N(R$_1$R$_2$);

when at least one X represents —NR$_1$R$_2$, —NR$_1$R$_2$ is a radical substituting at least one primary hydroxyl group and optionally at least one secondary hydroxyl group, attached to the cyclodextrin skeleton, in which R$_1$ and R$_2$ independently represent a linear or cyclic, saturated or unsaturated, hydroxylated or non-hydroxylated hydrocarbon radical containing 1 to 30 carbon atoms;

when at least one X represents —O—C(=O)—R, —O—C(=O)—R is a radical substituting at least one primary hydroxyl group, and optionally at least one secondary hydroxyl group, or the two, attached to the cyclodextrin skeleton, where R represents a linear or cyclic, saturated or unsaturated, hydroxylated or non-hydroxylated hydrocarbon radical containing 1 to 30 carbon atoms;

(X)$_y$ can represent a mixture of groups —NR$_1$R$_2$ and —OCOR substituting at least one primary hydroxyl group and optionally at least one secondary hydroxyl group, or the two;

M is a substituent for at least one primary or secondary alcohol function or the two of the cyclodextrin, M is a functional group G$_1$ or a specific radical G$_2$, either directly substituting a primary or secondary alcohol function of the cyclodextrin, or indirectly substituting said primary or secondary alcohol function via a spacer arm W, where:

when X is an amine, W is a spacer arm containing 1 to 20 carbon atoms, and includes a functional group selected from the group consisting of acid, sulfonic and phosphoric acid, alkanoyl, alkenyl, alkynyl, aldehyde, amine, amide, azide, acid anhydride, ketone, isocyanate, phenyl, hydroxyl, epoxy, ester, imide, amidine, halide, nitro, nitriles, peroxides, organometallic derivatives, and sulfur-containing derivatives, when X is an ester, W is a spacer arm containing 1 to 20 carbon atoms, and includes a functional group selected from the group consisting of acid, sulfonic and phosphoric acid, alkanoyl, alkenyl, alkynyl, aldehyde, amine, amide, azide, acid anhydride, ketone, isocyanate, phenyl, epoxy, ester, imide, amidine, halide, nitro, nitriles, peroxides, organometallic derivatives, and sulfur-containing derivatives, when X is an amine, G$_1$ represents at least one of the following functions and its derivatives: an acid, a sulfonic, a phosphoric acid, an alkanoyl, an alkenyl, an alkynyl, an aldehyde, an amine, an amide, an azide, an acid anhydride, a ketone, an isocyanate, a phenyl, a hydroxyl, an epoxy, an ester, an imide, an amidine, a halide, a nitro, a nitrile, a peroxide, an organometallic compound, and a sulfur-containing compound;

when X is an ester, G$_1$ represents at least one of the following functions and its derivatives: an acid, a sulfonic, a phosphoric acid, an alkanoyl, an alkenyl, an alkynyl, an aldehyde, an amine, an amide, an azide, an acid anhydride, a ketone, an isocyanate, a phenyl, an epoxy, an ester, an imide, an amidine, a halide, a nitro, a nitrile, a peroxide, an organometallic compound, and a sulfur-containing compound; and G$_2$ represents at least one compound selected from the group consisting of a sugar, a polyol, an oligosaccharide, a polysaccharide, a lectin, an amino acid, a peptide, a protein, an antibody, a nucleotide, a nucleoside, an oligonucleotide, an oligonucleoside, a chromophore, a polymer, a sterol, a steroid, a hormone, a flavonoid, a terpene, caffeine, theophylline, nicotinic compound, a vitamin, a vitamin ester, a cholesterol, a phospholipid, a glycolipid, a sphingolipid, a ceramid, a triglyceride, a natural polyphenol, a synthetic polyphenol, an essential oil, a flavoring, a fragrance, a dye, and a cosmetically active substance.

2. The method of claim 1, wherein R$_1$ and R$_2$ independently represent a linear or cyclic, saturated or unsaturated, hydroxylated or non-hydroxylated hydrocarbon radical containing 1 to 22 carbon atoms.

3. The method of claim 1, wherein R$_1$ and R$_2$ independently represent a fatty chain of 2 to 22 carbon atoms.

4. The method of claim 1, wherein when X represents NR$_1$R$_2$, 1% to 100% of the primary cyclodextrin hydroxyl groups are substituted by the amino group NR$_1$R$_2$.

5. The method of claim 1, wherein R represents a linear or cyclic, saturated or unsaturated, hydroxylated or non-hydroxylated hydrocarbon radical containing 1 to 22 carbon atoms.

6. The method of claim 1, wherein R represents a fatty chain that contains 2 to 22 carbon atoms.

7. The method of claim 1, wherein when X represents —O—COR, 1 to 100% of the primary hydroxyl groups of the cyclodextrins are substituted by the ester group —O—COR.

8. The method of claim 1, wherein the substituted cyclodextrin is in the form of nanoparticles.

9. The method of claim 1, wherein the substituted cyclodextrin is in the form of micelles.

10. The method of claim 1, wherein the substituted cyclodextrin comprises a cavity containing an active ingredient that is cosmetically acceptable, wherein the active ingredient is encapsulated therein, is covalently bonded therewith, or a combination thereof.

11. The method of claim 10, wherein the active ingredient is selected from the group consisting of at least one sugar, a polyol, an oligosaccharide, a polysaccharide, an amino acid, a peptide, a protein, a nucleotide, a nucleoside, an oligonucleotide, an oligonucleoside, a chromophore, a polymer, a sterol, a steroid, a hormone, a flavonoid, a terpene, caffeine, theophylline and their derivatives, nicotine and its derivatives, a vitamin, a vitamin ester, cholesterol, a phospholipid, a glycolipid, a sphingolipid, a ceramid, a triglyceride, a natural polyphenol, a synthetic polyphenol, an essential oil, a flavoring, a fragrance, and a dye, said substance being optionally admixed with a cosmetically acceptable excipient.

12. The method of claim 1, where the cyclodextrin is an α-cyclodextrin that is substituted by 1 to 18 lauric chains or 1 to 18 hexanoic chains or N,N-dipentylamine, at least one of said substituents being on at least one hydroxyl function of the primary base of the cyclodextrin.

13. The method of claim 1, wherein the cyclodextrin is a β-cyclodextrin that is substituted by 1 to 21 lauric chains or 1 to 21 hexanoic chains or N,N-dipentylamine, at least one of said substituents being on at least one hydroxyl function of the primary base of the cyclodextrin.

14. The method of claim 1, wherein the cyclodextrin is a γ-cyclodextrin that is substituted by 1 to 24 lauric chains or 1 to 24 hexanoic chains or N,N-dipentylamine, at least one of said substituents being on at least one hydroxyl function of the primary base of the cyclodextrin.

15. The method of claim 1, wherein the substituted cyclodextrin is further substituted by at least one substituent selected from the group consisting of 4-nitrophenylformate; ethyloxalate, chloroacetate, succinate, oxalate, sulfonate, and N-(2-aminoethyl)lactonamide.

16. The method of claim 1, wherein the substituted cyclodextrin is heptakis (6-deoxy-6-(N,N-dipentylamino))-β-cyclodextrin.

17. The method of claim 1, wherein the substituted cyclodextrin is a lauroate β-cyclodextrin.

* * * * *